US008889162B2

(12) United States Patent  
Patel et al.

(10) Patent No.: US 8,889,162 B2  
(45) Date of Patent: Nov. 18, 2014

(54) COSMETIC COMPOSITIONS CONTAINING POLYPROPYLSILSESQUIOXANE, A VOLATILE SOLVENT, BORON NITRIDE, AND SILICA

(75) Inventors: Sonal Patel, Iselin, NJ (US); Ashini Amin, Monroe, NJ (US); Lisa Voorhees-Nordhaus, Middlesex, NJ (US)

(73) Assignee: L'Oreal (FR)

( * ) Notice: Subject to any disclaimer, the term of this patent is extended or adjusted under 35 U.S.C. 154(b) by 534 days.

(21) Appl. No.: 13/076,924

(22) Filed: Mar. 31, 2011

(65) Prior Publication Data

US 2011/0243867 A1   Oct. 6, 2011

(51) Int. Cl.
*A61K 8/02* (2006.01)
*A61K 8/891* (2006.01)
*A61K 8/25* (2006.01)
*A61Q 1/10* (2006.01)
*A61K 8/19* (2006.01)

(52) U.S. Cl.
CPC . *A61Q 1/10* (2013.01); *A61K 8/891* (2013.01); *A61K 8/25* (2013.01); *A61K 8/0241* (2013.01); *A61K 2800/592* (2013.01); *A61K 2800/412* (2013.01); *A61K 8/19* (2013.01)

USPC .................. 424/401; 424/70.121; 424/78.03

(58) Field of Classification Search
CPC ......... A61K 8/0241; A61K 8/19; A61K 8/25; A61K 8/891; A61K 2800/412; A61K 2800/592; A61Q 1/10
See application file for complete search history.

(56) References Cited

U.S. PATENT DOCUMENTS

| | | | |
|---|---|---|---|
| 6,534,072 | B2 | 3/2003 | Mondet et al. |
| 7,250,159 | B1 | 7/2007 | Arnaud |
| 2006/0063014 | A1 | 3/2006 | Forray |
| 2006/0292096 | A1 | 12/2006 | Yu |
| 2007/0093619 | A1 | 4/2007 | Bui et al. |
| 2007/0243220 | A1* | 10/2007 | Sandewicz et al. ........... 424/401 |
| 2008/0171006 | A1 | 7/2008 | Bui et al. |
| 2008/0305061 | A1 | 12/2008 | Bui et al. |
| 2008/0305067 | A1 | 12/2008 | Bui et al. |
| 2009/0068255 | A1 | 3/2009 | Yu et al. |
| 2010/0034767 | A1* | 2/2010 | Trabelsi ..................... 424/78.03 |

* cited by examiner

*Primary Examiner* — Lezah Roberts  
*Assistant Examiner* — Nannette Holloman  
(74) *Attorney, Agent, or Firm* — Lerner, David, Littenberg, Krumholz & Mentlik, LLP

(57) ABSTRACT

Disclosed are cosmetic compositions containing a polypropylsilsesquioxane, a volatile solvent, boron nitride, and silica. Also disclosed are methods for making the cosmetic compositions and applying them to keratinous tissue such as skin in order to enhance its appearance.

18 Claims, No Drawings

COSMETIC COMPOSITIONS CONTAINING POLYPROPYLSILSESQUIOXANE, A VOLATILE SOLVENT, BORON NITRIDE, AND SILICA

CROSS-REFERENCE TO RELATED APPLICATIONS

This application claims the benefit of the filing date of U.S. Provisional Patent Application No. 61/319,520, filed Mar. 31, 2010, the disclosure of which is hereby incorporated herein by reference.

BACKGROUND OF THE INVENTION

The present invention generally relates to novel cosmetic compositions including eye shadow, and a method of use, including a method of making-up skin. More particularly, the present invention relates to an eye shadow compositions having a soft creamy feel with good product pick up, lay down, and high color impact and even coverage.

Conventional eye shadow compositions do not provide the desired aesthetics. The reason for this is that while commonly-used film-formers produce long wear, they produce brittle compositions that are difficult to pick up and lay down, and have a hard texture leading to an uneven application on the skin.

In addition, the hard and brittle nature of conventional eye shadow compositions produces a dry, hard texture. This texture makes conventional eye shadow compositions uncomfortable and irritating during application and wear.

Therefore, it is desirable to provide cosmetic compositions, in particular eye shadow compositions, having a soft creamy texture and long wear that are easy to pick up and lay down, have a high color impact, and produce even coverage.

SUMMARY OF THE INVENTION

A first aspect of the present invention is directed to a cosmetic composition, including an eye shadow composition, containing a polypropylsilsesquioxane, a volatile solvent, boron nitride, and silica.

A second aspect of the present invention is directed to a method of preparing a cosmetic composition, including an eye shadow composition, by mixing a polypropylsilsesquioxane, a volatile solvent, boron nitride, and silica.

A third aspect of the present invention is directed to a method of making up or enhancing the appearance of a keratinous tissue by applying to the keratinous tissue a cosmetic composition, including an eye shadow composition, containing a polypropylsilsesquioxane, a volatile solvent, boron nitride, and silica.

It has been surprisingly found that compositions according to an embodiment of the present invention have a creamy texture, excellent comfort and color impact, and good wear properties.

DETAILED DESCRIPTION

Other than in the operating examples, or where otherwise indicated, all numbers expressing quantities of ingredients and/or reaction conditions are to be understood as being modified in all instances by the term "about," meaning within 10% to 15% of the indicated number.

"Keratinous tissue", as used herein, includes but is not limited to, skin, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C. "Non-volatile", as used herein, means having a flash point of greater than about 100° C.

As used herein, the expressions "at least one", "a", and "an" mean one or more and thus include individual components as well as mixtures/combinations.

"Long wear" compositions as used herein, refer to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Hardness" as used herein, refers to the resistance of a composition to penetration. Hardness may be evaluated according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed.

Polypropylsilsesquioxane

According to the present invention, compositions comprising a polypropylsilsesquioxane are provided. The polypropylsilsesquioxane of the present invention is a silicone polymer containing predominantly trifunctional monomer units containing a propyl radical. Silicone polymers are described according to the various monomeric siloxane units which make up the polymer.

A silsesquioxane is a silicone polymer made up predominantly of trifunctional silicone monomer units. A trifunctional silicone monomer shares three oxygen atoms when the monomer is part of a polymer and can be represented as $RSiO_{3/2}$:

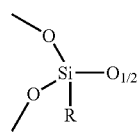

wherein R may be chosen from groups including alkyl groups, alkene groups, alkyne groups, hydroxyl groups, thiol groups, ester groups, acid groups, ether groups, phenyl groups, alkoxy groups. R may be further substituted. A silsesquioxane made up predominantly of trifunctional monomers in which R is a propyl radical is a polypropylsilsesquioxane.

The polypropylsilsesquioxane is present in the inventive compositions in amounts generally ranging from about 1 to about 30%, and in some embodiments from about 2 to about 20%, and in some embodiments from about 5 to about 15%, by weight, based on the total weight of the composition.

Volatile Solvent

The compositions of the invention also contain a volatile solvent capable of solubilizing the polypropylsilsesquioxane film former. The expression "volatile solvent" means any non-aqueous medium capable of evaporating on contact with the skin or the lips in less than one hour at room temperature and atmospheric pressure.

Representative examples of suitable volatile solvents include volatile hydrocarbon-based oils such as, for example, volatile hydrocarbon oils having from 8 to 16 carbon atoms and their mixtures and in particular branched C8 to C16 alkanes such as C8 to C16 isoalkanes (also known as isoparaffins), isododecane, isodecane, isohexadecane, and for example, the oils sold under the trade names of Isopar or Permethyl, the C8 to C16 branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

TABLE 2-continued

| Compound | Flash Point (° C.) | Viscosity (cSt) |
| --- | --- | --- |
| PDMS DC 200 (5 cSt) from Dow Corning | 134 | 5 |
| PDMS DC 200 (3St) from Dow Corning | 102 | 3 |

In an embodiment of the present invention the volatile solvent is cyclopentasiloxane.

The volatile solvent is present in the inventive compositions in amounts generally ranging from about 1 to about 30%, and in some embodiments from about 2 to about 20%, and in some embodiments from about 5 to about 15%, by weight, based on the total weight of the composition.

The polypropylsilsesquioxane and the volatile solvent may be obtained from commercial sources as a ready-made mixture. One example of a polypropylsilsesquioxane combined with a volatile solvent suitable for use in the present invention is commercially available from Dow-Corning as Dow Corning 670 Fluid (INCI: polypropylsilsesquioxane and cyclopentasiloxane). The polypropylsilsesquioxane of Dow Corning 670 Fluid has a general formula of $R_n SiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4%, by weight, preferably between 5 and 10%, by weight, and more preferably between 6 and 8%, by weight, based on the total weight of the composition. The volatile solvent of Dow-Corning 670 Fluid is cyclopentasiloxane. The polypropylsilsesquioxane and cyclopentasiloxane are generally present in about equal amounts.

Boron Nitride

According to the present invention, compositions comprising boron nitride are provided. Boron nitride provides creaminess to the cosmetic compositions. Boron nitride is generally present in the cosmetic compositions of the present invention in particulate form. Generally, the boron nitride has an average particle size of from about 1 µm to about 30 µm. In certain embodiments, the boron nitride has an average particle size of from about 2 µm to about 20 µm, and in other embodiments from about 5 µm to about 15 µm. Boron nitride is present in the inventive compositions in an amount generally ranging from about 1 to about 5%, and in some embodiments from about 2 to about 4%, and in some embodiments from about 2.5 to about 3.4%, based on the total weight of the composition.

Silica

According to the present invention, compositions comprising silica are provided. Silica provides dryness to the compositions of the present invention. Silica is generally present in the cosmetic compositions of the present invention in particulate form. Generally, the silica has an average particle size of from about 1 µm to about 10 µm. In certain embodiments, the silica has an average particle size of from about 2 µm to about 5 µm, and in other embodiments about 3 µm. Silica is present in the inventive compositions in an amount generally ranging from about 0.01 to about 5%, and in some embodiments from about 0.05 to about 2%, and in some embodiments from about 0.1 to about 1%, based on the total weight of the composition.

In an embodiment of the present invention, the boron nitride and silicone are present in a ratio that provides a balance between creaminess and dryness while resulting in a comfortable feel that maintains sufficient structure to allow for easy application and long wear. Typically, the cosmetic compositions of the present invention have a ratio of boron nitride to silica of from about 1:3 to about 40:1, in some embodiments from about 1:1 to about 10:1, in some embodiments from about 2:1 to 4:1, and in some embodiments from about 2.5:1 to about 3.4:1.

Optional Ingredients

Non-Volatile Solvent

The compositions of the present invention may contain a non-volatile solvent or oil. Exemplary non-volatile solvents or oils include cosmetically or dermatologically acceptable and, in general, physiologically acceptable oils, such as carbon-based, hydrocarbon-based, fluoro and/or silicone oils, of mineral, animal, plant or synthetic origin, alone or as a mixture. Representative examples of suitable non-volatile solvents or oils include synthetic esters and ethers, especially of fatty acids, for instance the oils of formulae $R^1COOR^2$ and $R^1OR^2$ in which $R^1$ and $R^2$ represent, independently of each other, a branched or unbranched hydrocarbon-based chain containing from 3 to 30 carbon atoms, for instance purcellin oil, isononyl isononanoate, isopropyl myristate, ethylhexyl palmitate (commercially available from Croda Chemicals as Crodamol OP), 2-octyldodecyl stearate, 2-octyldodecyl erucate, isostearyl isostearate or isononyl isononanoate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate (Prisorine 3631); linear or branched hydrocarbons of mineral or synthetic origin, such as volatile or non-volatile liquid paraffins, and derivatives thereof. Representative examples of silicone oils are methicone phenyl trimethicone, commercially available from Dow-Corning as DC 556, and caprylyl methicone, commercially available from Dow-Corning as FZ-3196. Further examples of non-volatile solvents or oils include polyalphaolefins, which include ethylene derivatives oligomerized into even-numbered carbon polyalphaolefins e.g., $C_6$-$C_{14}$ olefins such as polydecene and polymers of $C_6$, $C_8$, $C_{12}$ and C14 olefins. The polyolefins may have a molecular weight (MW) generally ranging from about 280 to about 11,500, and a viscosity (CPs at about 20° C.) generally ranging from about 7 to about 32,500. They may also be hydrogenated, for example, hydrogenated polyisobutene. In some embodiments, the non-volatile solvent includes PureSyn™ 2 (MW about 283), 4 (MW about 432), 6 (MW about 570), 8 (MW about 611), 150 (MW about 3980) and 300 (MW about 4870) (INCI name: hydrogenated polydecene). The viscosity of these polymers is about 8, about 33, about 64, about 103, about 4179 and about 8400, respectively.) PureSyn™ 100 (MW about 2939, viscosity about 3900, INCI name: hydrogenated C6-14 olefin polymers) and PureSyn™ 1000 (MW about 11,500, viscosity about 32,400, INCI name: polydecene) may also be useful. The PureSyn™ products are available from Exxon Chemicals.

A non-volatile solvent or oil, if present, is in amounts generally ranging from about 0.1% to about 70%, and in some embodiments, about 0.5% to about 40%, and in other embodiments, 1% to about 25%, based on the total weight of the composition.

Water

The compositions of the present invention may or may not include water. The compositions of the present invention are typically waterproof. The water content of waterproof cosmetic compositions generally ranges from about 0 to about 60% by weight, and in some embodiments from about 0 to about 35%, by weight, based on the total weight of the composition. In an embodiment of the present invention, the composition is anhydrous or substantially anhydrous, which refers to compositions having no added or additional water (i.e., water not part of another commercially available ingredient present in the composition), e.g., having a water content of less than about 5% by weight of the total composition.

Lipophilic Thickener

The cosmetic compositions of the present invention may contain a lipophilic thickener. Lipophilic thickeners may be chosen from gelling agents in polymeric form and gelling agents in mineral form. The gelling agent includes agents that gel via chemical reticulation and agents that gel via physical reticulation. Modified clays may be used as gelling agents, examples of which include hectorites modified with an ammonium chloride of a $C_{10}$ to $C_{22}$ fatty acid, such as bentonite modified with distearyldimethylammonium chloride, also known as quaternium-18 bentonite, such as the products sold or made under the names Bentone 34 and Bentone 38 VCG by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

A lipophilic thickener, if present, is in amounts generally ranging from about 0.01% to about 10% relative to the total weight of the composition. In certain embodiments, the lipophilic thickener is present in an amount of from about 0.1% to about 5%, by weight, in other embodiments from about 0.5% to about 2%, by weight, and in yet other embodiments at about 1%, by weight, based on the total weight of the composition.

Gelling Activator

The compositions of the present invention may contain a gelling activator that activates modified clay lipophilic thickeners. In an embodiment of the present invention, the gelling activator is propylene carbonate. Gelling activators are generally present in an amount from about 0.01% to about 5%, by weight, based on the total weight of the composition. A gelling activator, if present, is in amounts generally ranging from about 0.05 to about 2%, by weight, in other embodiments from about 0.1% to about 1%, by weight, and in yet other embodiments at about 0.25%, by weight, based on the total weight of the composition.

Colorant

The inventive compositions may also contain a colorant, e.g., pigment. Pigments may be chosen from the organic and/or mineral pigments known in the art. These pigments may be in the form of pigmentary powder or paste. They may be coated or uncoated.

The pigments may be chosen, for example, from Natural (mineral) pigments, organic pigments, lakes, pigments with special effects such as nacres or glitter flakes, and mixtures thereof.

Natural pigments may be chosen from, for example, iron oxides, mica (e.g., mica sericite), chromium oxides, manganese violet, ultramarine blue, titanium dioxide, chromium hydrate and ferric blue.

The organic pigment may be chosen from nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds.

White or colored organic pigments may be chosen from carmine, carbon black, aniline black, melanin, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

Examples that may also be mentioned include pigmentary pastes of organic pigments, such as the product sold by the company Hoechst under the names: Jaune Cosmenyl IOG: Pigment Yellow 3 (CI 11710); Jaune Cosmenyl G: Pigment Yellow 1 (CI 11680); Orange Cosmenyl GR: Pigment Orange 43 (CI-71105); Rouge Cosmenyl R: Pigment Red 4 (CI 12085); Carmine Cosmenyl FB: Pigment Red 5 (CI 12490); Violet Cosmenyl RL: Pigment Violet 23 (CI-51319); Bleu Cosmenyl A2R: Pigment Blue 15.1 (CI-74160); Vert Cosmenyl GG: Pigment Green 7 (CI 74260); Noir Cosmenyl R: Pigment Black 7 (CI 77266).

The pigments may also be in the form of composite pigments as described in EP 1 184 426. These composite pigments may be compounds of particles comprising a mineral core, at least one binder for ensuring the binding of the organic pigments to the core, and at least one organic pigment at least partially covering the core.

The organic pigment may also be a lake. The term "lake" means insolubilized dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate, and aluminium.

Among the dyes, mention may be made of cochineal carmine. Mention may also be made of the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 0 (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a non-uniform colored appearance (characterized by a certain shade, a certain vivacity and a certain lightness) that changes as a function of the conditions of observation (light, temperature, observation angles, etc.). They thus contrast with white or colored pigments that afford a standard uniform opaque, semi-transparent or transparent shade.

Several types of pigment with special effects exist: those with a low refractive index, such as fluorescent, photochromic or thermochromic pigments, and those with a high refractive index, such as nacres or glitter flakes.

Examples of pigments with special effects that may be mentioned include nacreous pigments such as white nacreous pigments such as mica coated with titanium or with bismuth oxychloride, colored nacreous pigments such as titanium mica with iron oxides, titanium mica with ferric blue or with chromium oxide, titanium mica with an organic pigment of the abovementioned type, and also nacreous pigments based on bismuth oxychloride. Nacreous pigments that may be mentioned include the Cellini nacres sold by Engelhard (mica-TiO$_2$-lake), Prestige sold by Eckart (mica-TiO$_2$), Prestige Bronze sold by Eckart (mica-Fe$_2$O$_3$), and Colorona sold by Merck (mica-TiO$_2$—Fe$_2$O$_3$).

In addition to nacres on a mica support, multilayer pigments based on synthetic substrates such as alumina, silica, sodium calcium borosilicate or calcium aluminium borosilicate, and aluminium, may be envisaged.

Mention may also be made of pigments with an interference effect that are not fixed onto a substrate, for instance liquid crystals (Helicones HC from Wacker), holographic interference flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known from the literature. They may be manufactured in particular according to the processes described, for example, in U.S. Pat. No. 6,225,198 or U.S. Pat. No. 5,990,479, in the publications cited therein, and also in the following publications: Dabboussi B. O. et al. "(CdSe) ZnS core-shell quantum dots: synthesis and characterization of a size series of highly luminescent nanocrystallites" Journal of Physical Chemistry B, vol. 101, 1997, pp. 9463-9475 and Peng, Xiaogang et al. "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that may be used makes it possible to obtain a wide range of colors, and also particular optical effects such as metallic effects or interference effects.

A colorant, such as a pigment, if present, is in amounts generally ranging from about 0.01% to about 50%, based on the total weight of the composition. In certain embodiments, the pigment is present in an amount of from about 1% to about 45%, by weight, in other embodiments from about 10% to about 40%, by weight, and in yet other embodiments from about 30% to about 40%, by weight, based on the total weight of the composition. In particular embodiments, the pigment is present in an amount of about 35%, by weight, based on the total weight of the composition.

Additional Polymers

The cosmetic compositions may contain additional polymers, e.g., film forming polymers that are compatible with the other ingredients and form a film after application. Suitable polymers include polyvinylpyrrolidones (PVP) and vinyl copolymers, e.g., vinyl pyrrolidone (VP)/hexadecane copolymer, PVP/hexadecene copolymer and VP/eicosene copolymer (e.g., Ganex V220, which is a trade name of ISP Inc. of Wayne, N.J.), trimethylsiloxysilicate and acrylates copolymer. An additional polymer, if present, is in amounts generally ranging from about 0.1% to about 20% by weight.

Wax

The cosmetic compositions of the present invention may contain a wax. As used herein, the term "wax" means a lipophilic fatty compound that is solid at room temperature about (25° C.) and atmospheric pressure (760 mm Hg, i.e., 105 Pa), which undergoes a reversible solid/liquid change of state and which has a melting point of greater than 30° C. and in some embodiments, greater than about 55° C. up to about 120° C. or even as high as about 200° C. For the purposes of the invention, the waxes are those generally used in cosmetics and dermatology. A variety of waxes may be useful, including waxes of animal origin, waxes of plant origin, waxes of mineral origin and waxes of synthetic origin. Representative examples of suitable waxes of animal origin include beeswaxes, lanolin waxes and Chinese insect waxes. Representative examples of suitable waxes of plant origin include rice waxes, carnauba wax, candelilla wax, ouricurry wax, cork fibre waxes, sugar cane waxes, Japan waxes, sumach wax and cotton wax. Representative examples of suitable waxes of mineral origin include paraffins, microcrystalline waxes, montan waxes and ozokerites. Representative examples of suitable waxes of synthetic origin include polyolefin waxes, e.g., polyethylene waxes, such as Polywax® 500 commercially available from baker Petrolite, waxes obtained by Fischer-Tropsch synthesis, waxy copolymers and their esters, and silicone and fluoro waxes. Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils. In some embodiments, the compositions contain at least two or at least three waxes. A wax, if present, is in amounts generally ranging from about 0.1% to about 20%, and in some embodiments from about 0.5% to about 15%, or from about 1% to about 10% by weight, based on the total weight of the composition.

Filler

The compositions of the present invention may contain a filler (e.g., lamellar or non-lamellar, inorganic or synthetic, colorless or white particles) other than boron nitride and silica. Representative examples of suitable fillers include mothers-of-pearl, mica, kaolin, iron oxides, titanium dioxide, polyamide powders, for instance nylon-12 and Nylon® (Orgasol from Atochem), poly-alanine powders, polyethylene powders, tetrafluoroethylene polymer powders, for instance Teflon®, starch, hollow polymer microspheres such as those of polyvinylidene chloride/acrylonitrile, for instance Expancel® (Nobel Industries), acrylic powders such as Polytrap® (Dow Corning), polymethyl methacrylates particles and silicone resin microbeads (for example Tospearls® from Toshiba), magnesium hydrocarbonate, hydroxyapatite, and glass and ceramic microcapsules. Mothers-of-pearl should be understood to mean iridescent particles produced especially by certain mollusks in their shell or else synthesized. Fillers may be in powderous form. Fillers are present in amounts generally ranging from about 0.1% to about 10%, and in some embodiments from about 0.2% to about 5% by weight, based on the total weight of the composition.

Preservative

The cosmetic compositions of the present invention may contain a preservative. Suitable preservatives include caprylyl glycol, sold under the trade name Octoil® by the company Dermosoft, alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben), and phenoxyethanol. Mixtures of preservatives are also useful, e.g., the mixture of methylparaben, ethylparaben, propylparaben and butylparaben sold under the name Nipastat by Nipa, the mixture of phenoxyethanol, methylparaben, ethylparaben, propylparaben and butylparaben, also sold by Nipa under the name Phenonip, and the mixture of phenoxyethanol, methylparaben, isopropylparaben, isobutylparaben and butylparaben, sold by ISP under the trade name Liquapar Optima. In an embodiment of the present invention the preservative is caprylyl glycol. The preservative may be present in an amount generally ranging from about 0.01% to about 15% by weight, based on the total weight of the composition.

The compositions of the present invention may further contain at least one further (e.g., cosmetically or dermatologically acceptable) ingredient, including additives and adjuvants, including, for example, moisturizers, water-soluble thickeners, humectants, anti-foam agents (e.g., simethicone, which is a fluid composition containing polydimethylsiloxane and silica), sunscreen agents (e.g., inorganic sunscreen agent, such as titanium dioxide and zinc oxide and organic sunscreen agents, such as octocrylene, ethylhexyl methoxycinnamate, and avobenzone), dispersion enhancing agents, fibers, chelators (such as EDTA and salts thereof, particularly sodium and potassium salts), antioxidants (e.g., BHT, tocopherol), essential oils, fragrances, and cosmetically active agents and dermatological active agents such as, for example, anti-inflammatory agents, vitamins, and trace elements. These ingredients may be soluble or dispersible in whatever phase or phases is/are present in the cosmetic composition (i.e., aqueous and/or fatty phase).

The compositions for application to keratinous tissue may constitute in particular a cosmetic or dermatological composition for protecting, treating, or caring for keratinous tissue, such as skin, hair, including eyelashes and eyebrows, and lips. In certain embodiments, the cosmetic compositions of the present invention are in the form of a an eye shadow, foundation, mascara, an eyeliner, a blusher, a lipstick, a lipgloss, a care base or balm for the lips, or a concealer product. The cosmetic compositions of the present invention may be applied to keratinous tissue by hand. Alternatively, or in conjunction therewith, they may be applied via an applicator such as a sponge, cotton, brush, or a puff of a natural or synthetic material. In addition, the applicator may be attached to or contained within a container that serves as a reservoir for the cosmetic composition.

It has been surprisingly found that compositions of the present invention have a unique a creamy texture, producing excellent comfort and color impact. The combination of a polypropylsilsesquioxane, a volatile solvent, boron nitride, and silica allows for the balancing of creaminess and dryness. Thus, the cosmetic compositions of the present invention are more comfortable than conventional cosmetic compositions during application and wear and allow for more even application and excellent color impact while maintaining good wear properties.

The following examples are intended to further illustrate the present invention. They are not intended to limit the invention in any way. Unless otherwise indicated, all parts are by weight.

EXAMPLES

Example 1

An eyeshadow composition of the present invention is described below.

| PHASE | INGREDIENT | AMOUNT (Wt %) |
|---|---|---|
| A1 | Ethylhexyl Palmitate | 24.45 |
|  | Disteardimonium Hectorite | 1.00 |
| A2 | Phenyl Trimethicone | 3.88 |
|  | Hydrogenated Polyisobutene | 6.62 |
|  | Ultramarines | 4.00 |
|  | Red Iron Oxides | 3.45 |
|  | Black Iron Oxides | 1.55 |
| A3 | Propylene Carbonate | 0.25 |
| B | Polyethylene | 6.00 |
| C | Nylon-12 | 0.50 |
|  | Boron Nitride | 2.50 |
|  | Silica | 1.00 |
| D | Mica and Iron Oxides and Titanium Dioxide and Ferric Ferrocyanide | 5.00 |
|  | Mica and Iron Oxides and Titanium Dioxide | 11.65 |
|  | Mica and Iron Oxides | 5.35 |
|  | Mica | 4.00 |
| E | Caprylyl Glycol | 0.30 |
|  | Polypropylsilsesquioxane (50%) and cyclopentasiloxane (50%) | 18.50 |
| Total |  | 100.00 |

The eyeshadow composition described above was prepared as follows. The ingredients of Phases A1 and A2 were combined and ground at 7,000 rpm of 15 minutes in a homogenizer. The propylene carbonate (Phase A3) was added to the mixture and mixed for an additional 3 minutes at 7,000 rpm to form a gel. The mixture was heated to 90° C. in an oil bath. The polyethylene (Phase B) was added while maintaining the temperature between 90° C. and 95° C. The mixture was mixed with a blade mixer for 15 minutes to ensure that the polyethylene was completely melted. With continued mixing, the ingredients of Phase C and then of Phase D were added. Mixing was continued until the ingredients were well dispersed. The ingredients of Phase E were added with continued mixing and the temperature maintained at between 80° C. and 85° C. The mixture was then poured into appropriate containers at a temperature between 80° C. and 85° C. and allowed to cool to room temperature.

Example 2

Three comparative eyeshadow compositions are described below.

| PHASE | INGREDIENT | AMOUNT (Wt %) Composition |  |  |
|---|---|---|---|---|
|  |  | 2A | 2B | 2C |
| A1 | Ethylhexyl Palmitate | 24.45 | 24.45 | 24.45 |
|  | Disteardimonium Hectorite | 1.00 | 1.00 | 1.00 |
| A2 | Phenyl Trimethicone | 3.88 | 3.88 | 3.88 |
|  | Hydrogenated Polyisobutene | 6.62 | 6.62 | 6.62 |
|  | Ultramarines | 4.00 | 4.00 | 4.00 |
|  | Red Iron Oxides | 3.45 | 3.45 | 3.45 |
|  | Black Iron Oxides | 1.55 | 1.55 | 1.55 |
| A3 | Propylene Carbonate | 0.25 | 0.25 | 0.25 |
| B | Polyethylene | 6.00 | 6.00 | 6.00 |
| C | Nylon-12 | 0.50 | 0.50 | 3.00 |
|  | Boron Nitride | 0.00 | 0.00 | 0.00 |
|  | Lauroyl Lysine | 0.00 | 2.50 | 0.00 |
|  | Silica | 0.00 | 1.00 | 1.00 |
| D | Mica and Iron Oxides and Titanium Dioxide and Ferric Ferrocyanide | 5.00 | 5.00 | 5.00 |
|  | Mica and Iron Oxides and Titanium Dioxide | 11.65 | 11.65 | 11.65 |
|  | Mica and Iron Oxides | 5.35 | 5.35 | 5.35 |
|  | Mica | 7.50 | 4.00 | 4.00 |
| E | Caprylyl Glycol | 0.30 | 0.30 | 0.30 |
|  | Polypropylsilsesquioxane (50%) and cyclopentasiloxane (50%) | 18.50 | 18.50 | 18.50 |
| Total |  | 100.00 | 100.00 | 100.00 |

To summarize, in Composition 2A, the boron nitride and silica of the composition of Example 1 were replaced with mica. In Composition 2B, the boron nitride of the composition of Example 1 was replaced with lauroyl lysine. In Composition 2C, the boron nitride of the composition of Example 1 was replaced with nylon-12.

Each of the comparative eyeshadow compositions described above was prepared using the procedure described in Example 1. The three comparative compositions were compared to the inventive composition of Example 1 for hardness, application, texture, and color impact.

Each of the comparative compositions and the inventive composition were evaluated for hardness as described above. Evaluations were made multiple times and the average hardness was calculated. The average hardness (i.e., peak force) for each composition is shown below.

| Composition | Average Hardness (Peak Force) g-force |
|---|---|
| Composition of Example 1 (n = 9) | 182.48 |
| Composition 2A (n = 9) | 261.11 |
| Composition 2B (n = 10) | 243.28 |
| Composition 2C (n = 10) | 256.95 |

In each case, the comparative composition has a hardness significantly higher than that of the inventive composition. The lower hardness of the composition of the present invention represents a softer, creamier product that has better product pick up, lay down, and coverage.

In addition, the inventive composition of Example 1 had the most color impact and even coverage of the four tested compositions. Composition 2A had a dry, uncomfortable texture. Compositions 2B and 2C had a streaky, uneven application with less coverage and color impact.

Example 3

An eyeshadow composition of the present invention is described below.

| PHASE | INGREDIENT | AMOUNT (Wt %) |
|---|---|---|
| A1 | Ethylhexyl Palmitate | 24.45 |
|  | Disteardimonium Hectorite | 1.00 |
| A2 | Phenyl Trimethicone | 3.88 |
|  | Hydrogenated Polyisobutene | 6.62 |
| A3 | Propylene Carbonate | 0.25 |
| B | Polyethylene | 6.00 |

-continued

| PHASE | INGREDIENT | AMOUNT (Wt %) |
|---|---|---|
| C | Nylon-12 | 0.50 |
|   | Boron Nitride | 2.50 |
|   | Silica | 1.00 |
| D | Mica and Titanium Dioxides and Iron Oxides | 21.00 |
|   | Mica and Titanium Dioxides | 4.00 |
|   | Mica Sericite | 10.00 |
| E | Caprylyl Glycol | 0.30 |
|   | Polypropylsilsesquioxane (50%) and cyclopentasiloxane (50%) | 18.50 |
| Total |  | 100.00 |

The eyeshadow composition described above was prepared as described in Example 1.

Example 4

An eyeshadow composition of the present invention is described below.

| PHASE | INGREDIENT | AMOUNT (Wt %) |
|---|---|---|
| A | Ethylhexyl Palmitate | 24.45 |
|   | Disteardimonium Hectorite | 1.00 |
|   | Phenyl Trimethicone | 3.88 |
|   | Hydrogenated Polyisobutene | 6.62 |
| A1 | Propylene Carbonate | 0.25 |
| B | Polyethylene | 6.00 |
|   | Caprylyl Glycol | 0.30 |
| C | Nylon-12 | 0.50 |
|   | Boron Nitride | 2.50 |
|   | Silica | 1.00 |
| D | Calcium Aluminum Borosilicate and Silver | 25.00 |
|   | Mica and Iron Oxides and Titanium Dioxide | 7.5 |
| E | Mica | 2.5 |
| F | Polypropylsilsesquioxane (50%) and cyclopentasiloxane (50%) | 18.50 |
| Total |  | 100.00 |

The eyeshadow composition described above was prepared as described in Example 1.

Example 5

An eyeshadow composition of the present invention is described below.

| PHASE | INGREDIENT | AMOUNT (Wt %) |
|---|---|---|
| A | Isododecane | 15.95 |
|   | Disteardimonium Hectorite | 1.00 |
|   | Phenyl Trimethicone | 7.5 |
|   | Caprylyl Methicone | 5 |
| A1 | Propylene Carbonate | 0.25 |
| B | Polyethylene | 6.00 |
|   | Caprylyl Glycol | 0.30 |
| C | Nylon-12 | 0.50 |
|   | Boron Nitride | 3.40 |
|   | Silica | 0.10 |
| D | Mica and Titanium Dioxide and Ferric Ferrocyanide | 25.00 |
|   | Mica and Iron Oxides and Titanium Dioxide | 7.5 |
| E | Mica | 2.5 |

| PHASE | INGREDIENT | AMOUNT (Wt %) |
|---|---|---|
| F | Polypropylsilsesquioxane (50%) and cyclopentasiloxane (50%) | 25.00 |
| Total |  | 100.00 |

The eyeshadow composition described above was prepared as described in Example 1.

Example 6

An eyeshadow composition of the present invention is described below.

| PHASE | INGREDIENT | AMOUNT (Wt %) |
|---|---|---|
| A1 | Ethylhexyl Palmitate | 24.45 |
|   | Disteardimonium Hectorite | 1.00 |
| A2 | Phenyl Trimethicone | 3.88 |
|   | Hydrogenated Polyisobutene | 6.62 |
|   | Red Iron Oxides | 0.98 |
|   | Yellow Iron Oxides | 0.30 |
|   | Titanium Dioxide | 2.10 |
|   | Black Iron Oxides | 1.62 |
|   | Mica | 5.00 |
| A3 | Propylene Carbonate | 0.25 |
| B | Polyethylene | 6.00 |
| C | Nylon-12 | 0.50 |
|   | Boron Nitride | 2.50 |
|   | Silica | 1.00 |
| D | Mica and Iron Oxides | 18.00 |
|   | Mica and Titanium Dioxides | 4.50 |
|   | Mica | 2.50 |
| E | Caprylyl Glycol | 0.30 |
|   | Polypropylsilsesquioxane (50%) and cyclopentasiloxane (50%) | 18.50 |
| Total |  | 100.00 |

The eyeshadow composition described above was prepared as described in Example 1.

Example 7

An eyeshadow composition of the present invention is described below.

| PHASE | INGREDIENT | AMOUNT (Wt %) |
|---|---|---|
| A1 | Ethylhexyl Palmitate | 24.45 |
|   | Disteardimonium Hectorite | 1.00 |
| A2 | Phenyl Trimethicone | 3.88 |
|   | Hydrogenated Polyisobutene | 6.62 |
|   | Red Iron Oxides | 0.04 |
|   | Yellow Iron Oxides | 0.11 |
|   | Black Iron Oxides | 0.62 |
|   | Mica | 3.23 |
| A3 | Propylene Carbonate | 0.25 |
| B | Polyethylene | 6.00 |
| C | Nylon-12 | 0.50 |
|   | Boron Nitride | 2.50 |
|   | Silica | 1.00 |
| D | Mica and Titanium Dioxides | 6.00 |
|   | Mica | 25.00 |
| E | Caprylyl Glycol | 0.30 |
|   | Polypropylsilsesquioxane (50%) and cyclopentasiloxane (50%) | 18.50 |
| Total |  | 100.00 |

The eyeshadow composition described above was prepared as described in Example 1.

Example 8

An eyeshadow composition of the present invention is described below.

| PHASE | INGREDIENT | AMOUNT (Wt %) |
|---|---|---|
| A1 | Ethylhexyl Palmitate | 22.45 |
|  | Disteardimonium Hectorite | 1.00 |
| A2 | Phenyl Trimethicone | 3.88 |
|  | Hydrogenated Polyisobutene | 6.62 |
|  | Red Iron Oxides | 1.25 |
|  | Yellow Iron Oxides | 1.57 |
|  | Titanium Dioxide | 5.55 |
|  | Black Iron Oxides | 0.63 |
| A3 | Propylene Carbonate | 0.25 |
| B | Polyethylene | 6.00 |
| C | Nylon-12 | 0.50 |
|  | Boron Nitride | 2.50 |
|  | Silica | 3.00 |
| D | Mica Sericite | 26.00 |
| E | Caprylyl Glycol | 0.30 |
|  | Polypropylsilsesquioxane (50%) and cyclopentasiloxane (50%) | 18.50 |
| Total |  | 100.00 |

The eyeshadow composition described above was prepared as described in Example 1.

Example 9

An eyeshadow composition of the present invention is described below.

| PHASE | INGREDIENT | AMOUNT (Wt %) |
|---|---|---|
| A1 | Ethylhexyl Palmitate | 24.45 |
|  | Disteardimonium Hectorite | 1.00 |
| A2 | Phenyl Trimethicone | 3.88 |
|  | Hydrogenated Polyisobutene | 6.62 |
| A3 | Propylene Carbonate | 0.25 |
| B | Polyethylene | 6.00 |
| C | Nylon-12 | 0.50 |
|  | Boron Nitride | 3.40 |
|  | Silica | 0.10 |
| D | Mica and Titanium Dioxides and Iron Oxides | 21.00 |
|  | Mica and Titanium Dioxides | 4.00 |
|  | Mica Sericite | 10.00 |
| E | Caprylyl Glycol | 0.30 |
|  | Polypropylsilsesquioxane (50%) and cyclopentasiloxane (50%) | 18.50 |
| Total |  | 100.00 |

The eyeshadow composition described above was prepared as described in Example 1.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition comprising:
   a) a polypropylsilsesquioxane;
   b) a volatile solvent;
   c) boron nitride; and
   d) silica;
wherein the boron nitride and silica are present in a ratio of about 2.5:1 to about 3.4:1, and wherein the composition is in the form of an eye shadow.

2. A composition according to claim 1, wherein the volatile solvent is selected from the group consisting of volatile hydrocarbon-based oils, silicone oils, and alcohols.

3. A composition according to claim 2, wherein the volatile solvent is selected from cyclopentasiloxane and isododecane.

4. A composition according to claim 1, further comprising a non-volatile solvent, a lipophilic thickener, a gelling activator, a pigment, a wax, a filler, and a preservative.

5. A composition according to claim 4, wherein the non-volatile solvent is selected from the group consisting of ethylhexyl palmitate, phenyl trimethicone, and caprylyl methicone.

6. A composition according to claim 4, wherein the lipophilic thickener is disteardimonium hectorite.

7. A composition according to claim 4, wherein the gelling activator is propylene carbonate.

8. A composition according to claim 4, wherein the filler is nylon powder.

9. A composition according to claim 4, wherein the wax is polyethylene.

10. A composition according to claim 4, wherein the preservative is caprylyl glycol.

11. The cosmetic composition of claim 1, comprising: the polypropylsilsesquioxane, cyclopentasiloxane, boron nitride, silica, ethylhexyl palmitate, phenyl trimethicone, disteardimonium hectorite, propylene carbonate, nylon powder, polyethylene, caprylyl glycol, and a pigment.

12. A method of making a cosmetic composition comprising mixing together:
   a) a polypropylsilsesquioxane;
   b) a volatile solvent;
   c) boron nitride; and
   d) silica;
wherein the boron nitride and silica are present in a ratio of about 2.5:1 to about 3.4:1, and wherein the composition is in the form of an eye shadow.

13. A method according to claim 12, wherein the volatile solvent is selected from the group consisting of volatile hydrocarbon-based oils, silicone oils, and alcohols.

14. A method according to claim 13, wherein the volatile solvent is selected from cyclopentasiloxane and isododecane.

15. A method according to claim 12, wherein the cosmetic composition further comprises a non-volatile solvent, a lipophilic thickener, a gelling activator, a pigment, a wax, a filler, and a preservative.

16. A method according to claim 12, wherein the cosmetic composition comprises a polypropylsilsesquioxane, cyclopentasiloxane, boron nitride, silica, ethylhexyl palmitate, phenyl trimethicone, disteardimonium hectorite, propylene carbonate, nylon powder, polyethylene, caprylyl glycol, and a pigment.

17. A method of making up or enhancing the appearance of keratinous tissue, comprising applying to keratinous tissue a cosmetic composition comprising:
  a) a polypropylsilsesquioxane;
  b) a volatile solvent;
  c) boron nitride; and
  d) silica;
wherein the boron nitride and silica are present in a ratio of about 2.5:1 to about 3.4:1, and wherein the composition is in the form of an eye shadow.

18. The composition of claim 1, wherein the polypropylsilsesquioxane is present in an amount from about 5 to about 15% by weight, the volatile solvent is present in an amount from about 5 to about 15% by weight, the boron nitride is present in an amount from about 1 to about 5% by weight, and the silica is present in an amount from about 0.1 to about 5% by weight, all weights being based on the total weight of the composition.

* * * * *